United States Patent
Miwa et al.

(10) Patent No.: US 6,653,293 B1
(45) Date of Patent: Nov. 25, 2003

(54) METHODS, APPARATUSES AND MEDICAMENTS FOR TREATING BODY FLUID RELATED DISEASES

(76) Inventors: Hirohide Miwa, 6-7-10, Miyazaki, Miyamaeku, Kawasaki-shi, Kanagawa-ken (JP); Masato Kino, 494-24-102, Nedo, Kashiwa-shi, Chiba-ken (JP)

( * ) Notice: Subject to any disclaimer, the term of this patent is extended or adjusted under 35 U.S.C. 154(b) by 0 days.

(21) Appl. No.: 08/139,693

(22) Filed: Oct. 22, 1993

(30) Foreign Application Priority Data

Oct. 23, 1992 (JP) ............................................. 4-285835
Sep. 16, 1993 (JP) ............................................. 5-230100

(51) Int. Cl.$^7$ ......................... A61K 31/70; A01K 38/00
(52) U.S. Cl. .......................................... 514/46; 514/12
(58) Field of Search ..................... 514/12, 46

(56) References Cited

U.S. PATENT DOCUMENTS

| | | | |
|---|---|---|---|
| 4,381,004 A | 4/1983 | Babb ...................... | 128/214 R |
| 4,824,432 A | 4/1989 | Skurkovich et al. ............ | 604/4 |
| 4,908,014 A | 3/1990 | Kroyer ........................... | 604/4 |
| 4,950,225 A | 8/1990 | Davidner et al. ............... | 604/4 |
| 5,037,649 A | 8/1991 | Balint, Jr. et al. ......... | 424/85.8 |
| 5,104,373 A | 4/1992 | Davidner et al. .............. | 604/4 |
| 5,116,307 A | 5/1992 | Collins .......................... | 604/4 |
| 5,192,264 A | 3/1993 | Fossel ........................... | 604/4 |

FOREIGN PATENT DOCUMENTS

| | | | |
|---|---|---|---|
| GB | 2189677 A | 11/1987 | ............ A61M/1/36 |
| JP | 63-240873 | 10/1988 | |
| JP | 63-240874 | 10/1988 | |
| JP | 63-252162 | 10/1988 | |
| JP | 2-274253 | 11/1990 | |
| JP | 3-188872 | 8/1991 | |
| JP | 4-342536 | 11/1992 | |

OTHER PUBLICATIONS

Forsdyke, 1991, Medical Hypotheses, 34(1) pp 24–27.*
Microbiology, 2nd Ed, 1973, Davis et al Ed, Harper & Pow, P468&1212.*
Ameisen, Jean Claude; Programmed Cell Death and Aids: From Hypothesis to Experiment, 1992, Immunology Today, vol. 13 No. 10, pp. 388–391.
Bisaccia, Emil et al.; Extracorporeal Photopheresis in the Treatment of Aids–Related Complex: A Pilot Study, Aug. 15, 1990, Annals of Internal Medicine, vol. 113 No. 4, pp. 263–264, 270–275.
Kobayashi, Nobuyuki and Nakanishi, Yoshinobu; HIV Infection and Cell Death, 1993, Experimental Medicine, vol. 11 No. 5, pp. 121(603)–128(610) including abstract.
Kobayashi, Nobuyuki and Nakanishi, Yoshinobu; Infection of Virus, Aids and Cell Death, 1993, Nikkei Science, pp. 34–41 including abstract.
Matsuyama, Toshifumi et al.; Cytocidal Effect Of Tumor Necrosis Factor on Cells Chronically Infected With Hyman Immunodeficiency Virus (HIV): Enhancement Of HIV Replication, Jun. 1989, Journal of Virology, pp. 2504–2509.
Pantaleo, Giuseppe et al.; HIV Infection iS Active and Progressive in Lymphoid Tissue During the Clinically Latent Stage Of Disease, Mar. 25, 1993, Nature vol. 362, pp. 355–358.
Embretson, Janet et al., Massive Covert Infection of Helper T Lymphocytes and Macrophages By HIV During the Incubation Period of Aids, Mar. 25, 1993, Nature, vol. 362, pp. 359–362.
Stricker, Raphael B.; Hematologic Aspects oF HIV Disease: Diagnostic and Therapeutic Considerations, 1991, Journal of Clinical Apheresis 6:106–109.
Kiprov, Dobri D. et al; Therapeutic Apheresis in Human Immunodeficiency Virus–Related Syndromes, 1990, Therapeutic Hemaphereisis in the 1990s No. 57, pp. 184–197.
Kojima, Eiji and Mitsuya, Hiroaki; Strategies Of Antiviral Therapy for Aids, 1993, vol. 11 No. 5, pp. 163(645)–175(654) including abstract.
Mitsuya, Hiroaki et al.; Molecular Targets for Aids Therapy, Sep. 28, 1990, Science, vol. 249, pp. 1533–1544.
Sandstrom, Eric G. and Kaplan, Joan C.; Antiviral Therapy in Aids Clinical Pharmacological Properties and Therapeutic Experience to Date, 1987, Drugs 34: pp. 372–390.

* cited by examiner

Primary Examiner—Russell Travers
(74) Attorney, Agent, or Firm—Finnegan, Henderson, Farabow, Garrett & Dunner, L.L.P.

(57) ABSTRACT

This invention relates to two methods treating such disease as AIDS. The first method includes administering the Trigger Factor such as TNF, which is defined as substance stimulating infected cells to increase HIV replication and hence subjecting the infected cells to death or the programmed death (apoptosis), further administering new-infection suppressor such as AZT and preferably inducer to migrate infected cells (lymphocytes) to the blood system from the lymphatic system, and then continuing extinction of the replicated HIVs by extracorporeal blood processing until all the infected cells die.

The second method includes administering electroconductive and/or magnetic microparticles on the surface whereon of which such infectiously adhesive substance to HIVs and infected cells as CD4 is coated, and killing HIVs/infected cells adhered to the microparticles by heating the microparticles with electromagnetic field (wave) applied externally to the patient.

16 Claims, 1 Drawing Sheet

METHODS, APPARATUSES AND MEDICAMENTS FOR TREATING BODY FLUID RELATED DISEASES

BACKGROUND OF THE INVENTION

1. Field of the Invention

This invention relates to treating body fluid-related diseases, where pathogenic microorganisms and cells infected by the microorganisms are mainly contained in the body fluid, particularly such retrovirus diseases such as AIDS.

2. Behavior of HIV

AIDS is the acronym for Acquired Immunodeficiency Syndrome, caused by Human Immunodeficiency Virus (HIV). The behavior of HIV must be reviewed as the basis of this invention.

HIVs and HIV-infected cells in human blood, seminal fluid, vaginal mucous, etc., are spread from exchange of HIV-infected blood or lymphatic fluid or from contact with infected mucous membrane, thereby establishing a new infection of AIDS.

Glycoprotein, gp120 developed on the HIV envelope in a large quantity, adheres to CD4 protein, developed on the cell membrane of certain leucocyte cells as T-4 helper lymphocytes, macrophage and dendritic cells. These cells are known as CD4 (positive) cells. Fusion of the HIV envelope with the CD4 cell membrane is carried out by gp41 on the HIV envelope. The HIV RNA and reverse transcriptase of the HIV are brought into the CD4 cell. The HIV RNA is reverse transcribed as a complement DNA (pro virus) by the reverse transcriptase, and the provirus-DNA is combined into the host CD4 cell DNA.

The host cell then replicates the HIV RNA from the provirus-DNA as if the provirus were part of its own DNA. It further generates corresponding protein, cuts the protein into HIV components with the protease and assembles the HIV components into a new HIV. New HIVs thus bud out from the host cell membrane, mature and isolate themselves as free HIVs from the host cell. This proliferation process is repeated. HIV cannot proliferate by itself without the host cell. After proliferation is repeated, the host cell dies, reportedly because the host cell membrane has broken. However, more probably, the host cell (infected cell) dies as a result of apoptosis or the programmed death, caused by such substances as TNF or anti-Fas antibody.

When HIVs or infected cells enter human body fluid, CD4 cells are infected and the infected cells replicate free HIVs in such body fluid as blood. Within 6 to 8 weeks, the immune mechanism of human body function forms antibody to HIV, and the HIVs in the blood almost disappear. This antibody is used to verify HIV infection. However, the number of CD4 cells in blood remains nearly equal to and a little less than that of a-healthy person, around 800~1,200/mm$^3$.

The newly infected HIV carrier then enters an asymptomatic latent period, which lasts about 5 to 10 years. During the latent, period, the number of HIVs and CD4 cells in the patient's blood will not increase substantially. The number of infected CD4 cells remains around 0.2~1.0% of the total CD4 cells in the blood.

The activity of HIV/infected cells has been thought to be low during the latent period. But it was discovered in March 1993 that most of the HIV-infected CD4 cells remain in lymphonodes throughout the latent period and that new infection progresses during that time. Anthony S. Fauci et al., "HIV infection is active and progressive in lymphoid tissue during the clinically latent stages of disease." *Nature*, Vol. 362, No. 6418 (Mar. 25, 1993); 355–358. The mechanism for this progressive pathology is not clear but assumed to be as follows. Healthy CD4 cells also present in a lymphonode may be infected from direct cell-to-cell contact with an infected cell. Gp120 developed on the infected cell adheres to CD4 of the healthy cell and cell fusion occurs to form a giant multinucleic cell. Healthy CD4 cells may also be infected with free HIVs generated from neighboring infected cells. As a result of cell-to-cell infection and death of the infected cell (from apoptosis or the like), the number of CD4 cells decreases at the rate of 50/mm$^3$ every year.

When the number of CD4 cells in the blood approaches 400~300/mm$^3$, HIV proliferation of the infected cells is activated by certain factors, and the number of HIVs and infected cells in the blood begins to increase. This stage of infection is described as AIDS Related Complex (ARC). The decrease in CD4 cells allows diseases that have been suppressed by the immune system until then an invasive opportunity. Such diseases include infections such as pneumocystis carinii, cytomegalovirus, candidosis, etc., and neoplasms such as Kaposi's sarcoma, non-Hodgkin's lymphoma, etc.

Almost 10% of AIDS patients also suffer from neuropathy. It has been reported but not definitively shown that macrophage, one of the CD4 cells existing in the brain, becomes infected and causes degeneration of the central nervous system, although the degeneration mechanism is not yet clear. Thus, HIVs and infected cells may exist in cerebrospinal fluid. It is also reported that dendritic cells are infected and exist in Langerhans cells under skin or tissue surfaces. Regardless, both infections may be introduced through the blood stream.

Once the number of CD4 cells in blood decreases below 200/mm$^3$, the ARC period has evolved into AIDS. Patients may die in about one year as a result of the dominant ARC enhanced by extreme decrease of CD4 cells in blood.

It is not clear what factor causes the transition from the asymptomatic, latent period to the symptomatic (ARC, AIDS) period. Recently, it was reported(*a) that such transition occurs two months after the spontaneous mutation of 12th base in V3 region of gp120. However, it is not probable that all infected cells are activated by the same mutation. So it is natural to assume a certain substance that the inventors of the present invention call Trigger Factor initiates and stimulates the activation of infected cells and induces the asymptomatic-to-symptomatic transition. The activated infected cells may again generate the Trigger Factor and accelerate the disease. The Trigger Factor may stimulate the proliferation control region of provirus-DNA, accelerate HIV replication and finally bring the host cells to death through the cell membrane breakage or apoptosis.

It is found in vitro that TNF, namely tumor necrosis factor (and/or anti-Fas antibody, etc.) causes coagulation of DNA of the infected T-4 lymphocytes about 3 hours after administration and further subjects the infected cells to death(*b), and that HIV replication is highly stimulated during the process. TNF is not found in blood during the asymptomatic, latent period, but found during the symptomatic (ARC, AIDS) period. TNF could be one of the Trigger Factors defined by the inventors of the present invention. It is assumed(*c) that the infected cells may die following the program incorporated by human body defense system,—apoptosis. TNF (or anti-Fas antibody, etc.) is now the subject of research in this line.

3. Chemical Treatment—Prior Art

Development of vaccine has been unsuccessful, because the identifying target of the vaccine, gp120, is subject to very rapid mutation, more specifically in V3 region, resulting in too much variety of HIV stocks (quasi-HIV species).

Various medicines are under development, inhibiting various stages of HIV infection and proliferation such as adhesion to CD4, fusion into the host cell, reverse transcription, insertion into DNA, RNA replication, protein generation, dividing the protein into components, assembling the components, budding, maturing, etc. Ten or more medicines are reported successful in vitro, but none of them has been successful in vivo. Either they have not worked or have exhibited strong toxicity as a side effect to medication. Exceptions are AZT, ddI, ddC as reverse transcription inhibitors, but they are effective only in extending the amount of time before death and also show toxicity in long-term administration, and drug-resistant HIV stocks to them are found.

4. Extracorporeal Blood Processing—Prior Art

Incurability of AIDS by chemical treatment has led to development of various means of extracorporeal removal, inhibition or destruction of the blood borne HIVs and infected cells. Such means originate from the technology used for conventional disease like cancer, type-B hepatitis and lymphocyte-related illnesses.

The following modes are disclosed for the extracorporeal blood processing to treat AIDS.

Processing as whole blood.

Separating into two fractions, plasma fraction and blood cell fraction and then processing the plasma fraction. This is the so-called plasmapheresis.

Separating the white blood cells and plasma fraction from the red cell fraction, after which the former fraction is processed.

Separating the leukocyte (white blood cell) fraction from the red cell fraction, after which the leukocyte fraction is processed.

Processing blood is expected to influence other body fluid systems such as lymphatic system because of intracorporeal exchange between the blood and all the other body fluids (*m).

Administering heparin before the process to induce lymphocyte migration from the lymph system into the blood system(*n)(*p).

Already disclosed practical methods of the extracorporeal processings of AIDS are reviewed following the classified items shown in our Japanese patent application, Hei4-285835.

Electromagnetic wave.

Whole blood/fraction; UV, Sun spectrum light(*m)

Leukocyte fraction; UV, Laser(*n)

Radiation.

Leukocyte fraction; X-ray(*n)

Chemicals, Pharmaceuticals

Strong inactivation agent(*k) (*m) (No actual agent is presented.)

Formaldehyde(*m)

Diethyl ether(*q)

Oxidized/peroxidized lipoprotein(*r)

$ClO_2$, $Cl_2O_3$(*h)

Photochemical reaction with psoralen(*d)

Adsorption, adhesion, phase transition

Whole blood: Immunoadsorption column(*l)(*o)

Whole/fraction: Infectious adhesion column (No prior art)

Plasma or serum: Compounding virus with water-soluble high polymer substances having cation base such as polyvinyl pyridinum and transferring to solid phase.(*j)

Heating

Whole blood; 41~42.5° C., 1~4 hrs.(*n)

Whole blood; 38~45° C.(*f)

Whole blood; 56° C., 30 min.(*g)

Plasma; 40~70° C.(*e)

Leukocyte fraction; 39° C. for immunostimulation(*m)

Red cell fraction; 43° C. for killing virus(*m)

Whole blood; 41~42.5° C., pH=7.1~7.3(*p)

Pressure

Whole blood; 2000 atm, 2° C.~5000 atm, 25° C.(*i)

Acoustic vibration, mechanical shear

Whole blood; mechanical shear(*n)

Acoustic vibration (no prior art)

Electric current

Whole blood or fraction: generating Ag ion from Ag electrode and sterilizing pathogenics with the ion (*s).

Electromagnetic field (no prior art)

Such anticoagulants as heparin, dextran, natrium nitrate, natrium citrate, etc., and/or such volume extender (thinner) as saline are infused after blood is withdrawn. Neutralizing the anticoagulant and/or removing excess saline by dialysis or diuresis are disclosed.

Removing or neutralizing excess agents and toxic substances generated during the process and conditioning temperature, pH, electrolytes, etc., are also disclosed as the post processing.

REFERENCES

*a Shinichi Oka, Tokyo Medical Science Institute, *NHK News*, August 1993.

*b Nobuyuki Kobayashi, "Infection of Virus, AIDS, and Cell Death," *Nikkei Science* June 1993: 34–41 and "HIV Infection and Cell Death," *Experimental Medicine* Vol. 11, No. 5 (1993): 121–29.

*c Jean Claude Amelsen, "Programmed Cell Death and AIDS," *Immunology Today* 13 (1992): 388–91.

*d Emile Bisaccia et al., "Extracorporeal Photopheresis in the Treatment of AIDS Related Complex," *Annals of Internal Medicine* 113 (1990): 270–75.

*e Japan Laid-open Pat., Sho63-240873 3/1987, Joh et al.

*f Japan Laid-open Pat., Sho63-240874 3/1987, Joh et al.

*g Japan Laid-open Pat., Sho63-252162 4/1987, Ura.

*h Japan Laid-open Pat., Hei2-274253 2/1990, Camen et al.

*i Japan Laid-open Pat., Hei3-188872 12/1989, Iwakura et al.

*j Japan Laid-open Pat., Hei4-342536 3/1991, Onishi et al.

*k U.S. Pat. No. , 4,381,004 January/1981, Babb.

*l U.S. Pat. No. , 4,824,432 March/1986, Skurkovich et al.

*m U.S. Pat. No. , 4,908,014 September/1988, Kroyer.

*n U.S. Pat. No. , 4,950,225 September/1988, Davidner et al.

*o U.S. Pat. No. , 5,037,649 January/1989, Balint, Jr., et al.

\*p U.S. Pat. No. , 5,104,373 July/1990, Davidner et al.
\*q U.S. Pat. No. , 5,116,307 July/1990, Collins.
\*r U.S. Pat. No. , 5,192,264 October/1990, Fossel.
\*s U.K. Pat. Appli. 2 189 677A April/1986, Swift 5. Problems of Prior Art Chemical treatment has not yet succeeded. Such reverse transcription inhibitors as AZT, ddI, ddC can only delay death.

Extracorporeal blood processing has been introduced as a compelling need but has not yet been successful either. Blood processing can remove, inactivate or kill the HIVs and infected cells in blood. However, infected cells especially stay or stick to some tissue in lymphonodes, brain, etc., and their migration into the circulatory system will not be so great as expected with the administration of heparin. Most of the infected cells will stay outside of the blood stream and cannot be effectively processed with the extracorporeal blood processing only.

SUMMARY OF THE INVENTION

1. The First Method

The first method includes:

administering such Trigger Factor as TNF, anti-Fas antibody, which stimulate the proliferation control region of provirus—DNA in the infected cell—to increase proliferation rate, shorten the cell life (up to the programmed death or apoptosis) and causing the transition from latent period to ARC-AIDS period and also administering such new-infection suppressors or reverse transcription inhibitors as AZT, ddI or ddC against the proliferated free HIVs during the apoptosis process and administering as required certain agent such as heparin to induce migration of the infected cells from lymphatic system to circulatory system; and continuing extracorporeal blood processing to kill or remove free HIVs in blood until all the infected cells die away.

The necessary processing time will be 10~24 hours, as the DNA coagulation of the infected cell is recognized in three hours after contact with TNF. Therefore, larger dose of TNF, AZT, etc., in such a short amount of time will be allowed.

It is sufficient to process only free HIVs in blood, but it is also preferable to kill or remove infected cells in blood. This processing of infected cells can shorten the necessary processing time and reduce possibility of new infection.

This treatment is preferably applied to a patient in the latent period but can be applied to a patient in ARC and AIDS period, where the dosage of Trigger Factor may be reduced or omitted, as the Trigger Factor has already been developed in the patient by AIDS.

New methods of extracorporeal blood processing by the inventors are presented as shown below; however, the extracorporeal blood processing can be a prior art.

Pharmaceuticals effective in vitro selectively to infected cells but not yet allowed in vivo administration are listed.

Trigger Factor can be proposed as well to use for the extracorporeal processing of infected cells if the pharmaceuticals, cited above are not effective. Surviving liquid, saline plus cell-cultivating agents, is used as carrier liquid. In this case, the proliferated free HIVs existing in the liquid are easily separated by filtration and rendered to such killing process as heating. The liquid can be used recirculating after the killing process.

Infectious adhesion between gp120 of HIVs/infected cells and CD4 is utilized to remove HIVs/infected cells instead of immunoadsorption, which is not effective to HIVs because of very rapid mutation and resulted variety of the stocks. Complexed with a certain high polymer or adhered to CD4-coated electroconductive or magnetic-particles, HIVs and infected cells are modified and removed by transition from the liquid phase to the solid phase through filtration, centrifugation or electromagnetic force.

Heating to higher temperature in a very short time similar to milk pasteurization with microwave device, for example, is disclosed.

Acoustic vibration, yielding mechanical shear, cavitation and heating with an ultrasound device are also presented for killing and inactivating HIVs and infected cells.

Periodically, polarity-changed DC or AC current is used to generate $Cl_2$ or the others from NaCl, KCl in blood, and the $Cl_2$ or the others are used to kill HIVs and infected cells.

Electromagnetic wave is used to resonate the intramolecular oscillation of HIVs or infected cells and destroy them.

The wave is also used to remove or heat the CD4-coated electroconductive or magnetic particles on the surface of which HIVs and infected cells are adhered.

2. The Second Method

The second method includes:

administering the electroconductive and/or magnetic micro particles, coated with such infectiously adhesive substance as CD4 to HIVs and infected cells; and killing the HIVs and infected cells adhered to the micro particles by heating the micro particles with electromagnetic wave applied externally to a patient.

DESCRIPTION OF THE PREFERRED EMBODIMENTS

This invention relates to treating body fluid-related diseases, more particularly such retrovirus diseases as AIDS. The preferred embodiments are described on AIDS treatment, but the scope of this invention is not limited to AIDS.

Figure 1:
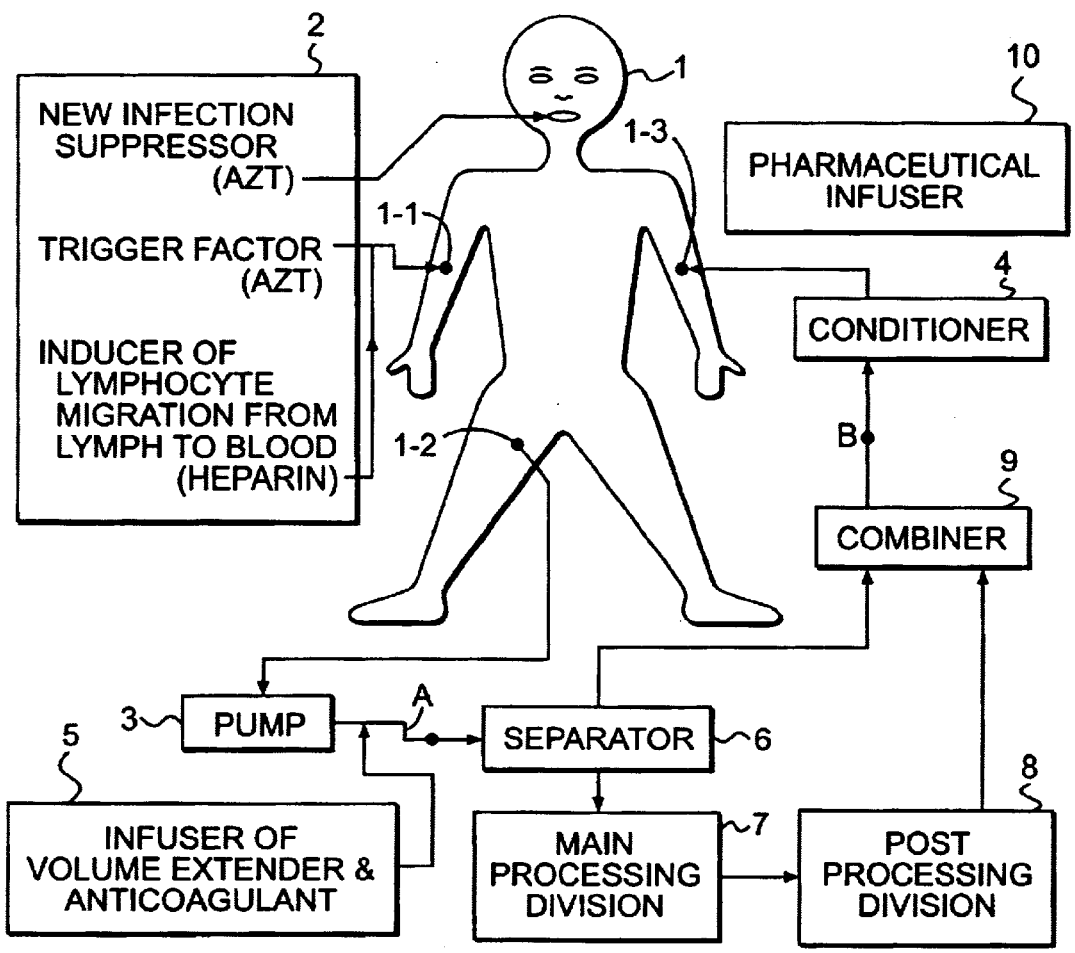
FIG. 1 shows a conceptual block diagram of a preferred embodiment of the first method of this invention.

The first embodiment will be described hereafter for the first method of this invention. FIG. 1 shows a conceptual block diagram, consisting of the means currently available and the facts well proven. 1 is an AIDS patient. 1-1 and 1-3 are veins. 1-2 is an artery or a vein. 2 presents pharmaceuticals consisting of such Trigger Factors as TNF or anti-Fas antibody, such new-infection suppressor as AZT, and, preferably such an inducer of lymphocyte migration from the lymphatic system to the blood system; as heparin. The heparin also works as an anticoagulant during the extracorporeal blood processing. Such pharmaceuticals are administered preliminarily and/or in parallel to the processing, intravenously or orally (AZT). It is preferable to administer TNF after AZT has developed sufficiently in blood to minimize new infection. Several hours after the administration, each concentration will reach sufficient value. When infected cells, such as T-4 lymphocytes, contact TNF, their DNA begins to coagulate after 3 hours and further breaks into fragments. After 10 to 24 hours, the infected cells die. During the process up to the death, the infected cells are stimulated to increase HIV replication and produce numbers of free HIVs. AZT inhibits new-infection by the free HIVs.

High body temperature a side effect of TNF may also decrease activity of free HIVs. To suppress the free HIV release from the stimulated infected cells, some agents will be also effective although they have not been developed yet. Free HIVs exist in blood, lymphatic fluid, cerebrospinal fluid, etc., and have intermobility between the body liquids or exchangeability. Free HIVs in all the body liquids can be killed or removed by the extracorporeal blood processing.

Free HIVs still remain theoretically in a minute quantity, even after the extracorporeal blood processing. However, as has been established, HIV antibodies already must exist particularly during the latent period based from the number of free HIVs in blood upon infection reaches maximum then decreases to the minute level of the latent period in about 2 months. These HIV antibodies are available to kill the remaining free HIVs. If some new HIV-stocks, just generated by mutation, are included in the remaining HIVs, administration of AZT, etc., in the following two months should be continued to prevent new-infection of cells and permit the formation of antibodies against the new stocks.

Blood is withdrawn through an appropriate vehicle, such as a cannula, from 1-2, the femoral vein (or artery). 3 is any type of suitable pump such as a conventional roller pump. 5 is any type of suitable infuser of such volume extender as saline and such anticoagulant as heparin, provided as necessary. The volume extender will compensate the blood volume loss held in the processing detour route and also be effective to decrease blood viscosity for easy handling. 6 is any kind of suitable separator which separates the whole blood into two fractions, namely the plasma fraction and blood cell fraction. A plasma separator used in the blood dialysis of a conventional artificial kidney can be used. This is a continuous flow process and is smaller and more convenient than centrifugation. Also, separation method of the prior art can be used. The blood cell fraction is fed to any kind of suitable combiner 9 without any processing. The plasma fraction is fed to the main processing division 7, where free HIVs are killed or removed. 8 is the post-processing division, where added agents, generated toxic substance, etc., are removed or neutralized. Various prior arts can be used in the processings at 7 and 8, such as heating at 40~70° C., UV irradiation, etc., and those described above. The processed plasma fraction is fed to the combiner 9 and combined with the blood fraction to form whole blood. The thus combined whole blood is fed to a suitable conditioner 4, where temperature, electrolytes, pH, etc., are conditioned and reinfused to the patient through 1-3. The drug infuser 10 is provided as required to supplement TNF, AZT, etc., if they are destroyed or removed in the main processor 7.

Replacing pathogenic fraction with a healthy one could be another main processing step.

Free HIV killing by the extracorporeal blood processing must be continued until all infected cells die. The duration will be 10 to 24 hours. The speed of killing must exceed the speed of free HIV proliferation by existing infected cells during the process, so a large volume of blood flow is preferable in the detour. Blood withdrawn at the femoral vein (or artery) and reinfused to the femoral vein or plural arm veins is contemplated. Saline water used as volume extender can be removed by small dialysis device provided in the post-processing division 8 or by administering a diuretic to the patient.

Figure 2:
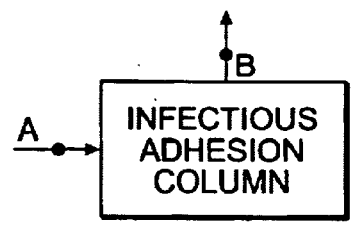
FIG. 2 shows the more preferable processing division, as an alternative of the processing divisions from A to B in FIG. 1.

The alternative processing division 11, which is simpler and more preferable but leaves some development to be desired, is shown in FIG. 2 instead of the processing divisions 6, 7, 8 and 9 in FIG. 1.

11 is essentially an infectiously adhesive bed such as a column, where plastic beads coated with CD4, for example, are packed. Strong infectious adhesivity between CD4 and gp120 of HIV and infected cell is utilized. Beads, fibers, membrane, etc., of glass, silica, plastic, etc., or other suitable materials coated with CD4 or T lymphocytes of a rabbit or a mouse, developing human CD4, can be used as an adhesion bed. Free HIVs (infected cells also) are removed from even the whole blood by strong selective adhesion to CD4. Because no agent is added and no toxic substance is generated., filtration of solids (possibly released from the beds) and coagulated blood is only necessary in the post-process 8.

High molecular weight polymers, having such cation base as polyvinyl pyridinium which forms a complex with virus, can be coated on the beads, etc., and be used as HIV-removing column through the HIV transition from the liquid phase to the solid phase.

Adding some electroconductive, magnetic particles or plastic particles larger than blood cells, coated with such adhesive substance as CD4 and removing the particles, having HIV and infected cells adhered to, with electromagnetic force, filtration or centrifugation can be used as another method of removing HIVs and infected cells.

Trigger factor is defined as a certain substance which may stimulate the region of proliferation (replication) control in the provirus (DNA) in an infected cell to increase proliferation (replication) rate, shorten the cell life (up to the programmed death or apoptosis) and cause the transition from the latent period to ARC-AIDS periods. The substance can exist in many forms which can be identified by comparing the blood in the latent period with the blood in the ARC-AIDS period. TNF or anti-Fas, antibody subjects the infected cells to programmed death (apoptosis) and high HIV replication (proliferation) rate and can be one of the Trigger Factors. The inventors also include as Trigger Factors some pharmaceuticals that may develop similar functions, namely cell death and increased replication rate for infected cells.

New-infection suppressors, such reverse transcription inhibitors as AZT (ddI, ddC), are used in FIG. 1. In addition, such an infectious adhesion inhibitor as soluble CD4 can be administered to neutralize gp120 of HIVs and infected cells. Some means to raise body temperature can be used to decrease HIV activity. Pharmaceuticals to raise body temperature include biochemical agents induced by malaria, typhoid, etc., or even pathogenic microorganisms themselves causing fever. Such artificial heating means as hyperthermia, extracorporeal blood heating, etc., also can be used. Processing time will be so short that higher dosage of TNF, AZT, etc., or otherwise intolerable conditions may be allowed.

Heparin is used in FIG. 1 as inducing means to migrate infected cells from the lymphatic system to the circulatory system, but PAS, dilantin, mesantoin, etc., also can be used. Such trigger factors as TNF or anti-Fas antibody can cause infected cell migration by stimulation. Such pathogens as viruses or microorganisms, which are less harmful than HIV and for which treatment is established, can be administered to induce lymphocyte migration to the blood system. Diseases having this function include infectious mononucleosis, pertussis, virus diseases (measles, rubella, varicella, mumps, roseola infantum and cytomegalovirus), Gram-negative bacilli infectious diseases (typhoid, paratyphoid fever and brucellosis), rickettsia, toxoplasmrosis, etc.

The following inducing means can also be used. Electro-conductive or magnetic micro particles coated with such adhesive substance to HIVs/infected cells as CD4 are administered. After HIVs/infected cells have adhered, electromagnetic field (static, alternative, pulsive, etc., of known parameters) is applied externally to the patient. The electromagnetic force liberates particles with infected cells adhered to from the staying or sticking tissue and induces them to migrate into the blood system. The particle size must be small enough, for example 1~5 micrometers, to go through the capillary vessel and reach the lymphatic system. The material of the particle must be harmless to the-human body. They are, for example, carbon, graphite, aluminum, silver, gold or stainless steel for electroconductive particles and ferrite, iron oxide for magnetic particles. Plastic micro particles of very uniform diameter are available in the market and are preferable to coat with metal by chemical plating, vacuum evaporation and with ferrite by reactor method.

Heating a particular part of the body such as a lymph node or the entire body by focusing or bulk heating means of heat conduction, microwave hyperthermia or vibrating with ultrasound can liberate infected cells as well. Ultrasonic irradiation of the entire body can be performed by immersing the body in a water tank.

TNF can diffuse, migrate and reach all parts of the patient including such HIV-present-region as in the body fluids, mucous and the central nervous system and subjects infected cells to stimulated replication and death. The free HIVs replicated by the TNF stimulation can move freely through the entire body as a result of the HIVs very small size. Killing or removal of the free HIVs will be accomplished through the processing of blood alone at the extracorporeal detour. However, cerebrospinal fluid could be an exception because of a gate to the brain, possibly necessitating extracorporeal processing of the cerebrospinal fluid drawn by intervertebral puncture and later reinfusion.

The method of the main processing in FIG. 1 can be any one of the prior arts already referred. The inventors of this invention also present a new method of processing as follows.

Heating at a temperature as high as 60~70° C. for no more than several seconds and using a method similar to pasteurization is intended to kill HIVs without damaging any blood components. Such heating can be realized by the plasma or whole blood stream passing through microwave field (for example 2450 MHz used for cooking). Rapid, uniform heating is realized simply as the heat is generated volumetrically in the fluid itself ($H_2O$, etc.), which differs from thermal conduction of the prior art. So critical temperatures can be used.

Flowing electric current can kill HIVs. Electrodes facing each other are placed in plasma or the whole blood. Saline can be added as an additional electrolyte. The electrode is preferably formed in metal mesh composed of such materials inert in blood as carbon, gold or platinum. By configuring the metal into mesh, the surface area is increased that will contact with body fluids. Electric current of polarity inverting DC in time or. AC is applied between the electrodes, which generates $Cl_2$ or other electrolytes by electrolyzing NaCl, Kcl etc., in blood. The $Cl_2$ or others generated near the electrodes kill HIVs and infected cells. They are restored to NaCl, KCl at polarity change or while passing out of the electric current region for reinfusion.

Applying ultrasound wave to the processor tank generates locally changing high frequency oscillation, mechanical shear with the surrounding viscous fluid, cavitation and heating as a result of viscoelasticity. Thus the generated effect can be used to kill HIVs.

Electromagnetic waves can resonate with the intramolecular vibration specific to the HIV/infected cells to destroy them. Electroconductive/magnetic particles, coated with CD4, etc., can be heated by electromagnetic fields to subject HIVs/infected cells to death adhering to the surface of the particles.

As explained heretofore, it is sufficient to remove or kill only free HIVs in the extracorporeal blood processing, and it is not necessary to kill, inactivate or remove infected cells because TNF attacks infected cells anywhere in the body. However, it is preferable to process the infected cells also extracorporeally to minimize the HIV replication and new-infection possibility despite the complexity and expense of the processing device.

The infected cell processing at the extracorporeal detour is disclosed hereafter.

Infected cells only should be attacked. Infected cells must be differentiated from healthy cells. No such pharmaceuticals have been disclosed in prior arts. The inventors of the present invention recognize the pharmaceuticals that selectively and effectively kill or inactivate infected cells in vitro but are not to be used because of non-efficacy or toxicity in vivo. Examples are:

| | |
|---|---|
| M-HDA | (Meiji Nyugyou) |
| GLQ223 | (Genelabs) |
| sCD4-IgG | (Genentic) |
| sCD4-PE40 | (Upjohn) and |
| Ro24-7429 | (Hoffman-La Roche). |

Infected cells are killed or inactivated irreversibly at contact with these pharmaceuticals. That is, the cells cannot revive even if these pharmaceuticals are removed later. Thus, the post processing of removing the pharmaceuticals from the blood cells and washing the blood cells with saline can be utilized before reinfusion to avoid toxicity from the pharmaceuticals. In this processing, separation to the blood fractions is preferable because later pharmaceutical removal is easier. The blood fraction is thinned with saline containing cell-cultivating substance—surviving liquid for cells. The pharmaceuticals are added into the surviving liquid.

If the pharmaceuticals listed above cannot be used, such trigger factors as TNF or anti-Fas antibody, can be used in the extracorporeal processing of infected cells. TNF can be added to the surviving liquid to subject the infected cells selectively to stimulated HIV replication and then to death. The generated free HIVs can be removed with the rapidly circulating mixture of the surviving liquid and TNF through filtration. The mixture can be sterilized with heat, UV, etc., and reused again. Such replication inhibitor as cycroheximid, achinomycine D, etc.(*c), can be added as this process is in vitro, and they can be removed at the post processing.

Commercially available leukocyte separator, such as IBM2997, can be used as the separator 8 in FIG. 1.

The preferred embodiment of the second method of this invention is described hereafter.

Electroconductive and/or magnetic micro particles of 1~6 micrometers in diameter are prepared, and their surface is coated with an agent that will adhere to HIV/infected cells such as CD4. Such details as materials used and method of production have already been described in the 14th paragraph of this Description of the Preferred Embodiment, and are not repeated herein.

The particles are suspended in saline and administered intravenously to a patient. The particles are small enough that they can diffuse and migrate into the blood system, capillary vessels and lymphatic system, etc. Being covered with CD4, the particles may not be attacked by such immune system as phagocyte. The particles adhere to HIVs and infected cells developing gp120, with infectious adhesion.

Alternating electromagnetic field (wave) of appropriate frequency is applied externally to the patient to heat the particles. Electromagnetic induction current is preferable to heat electroconductive particles. The frequency may be 20~1000 MHz as 1~5 MHz is used to heat 100 micrometer wire. 2450 MHz used for a microwave oven is not adequate as biotissue consisting of water and organic molecules is heated by electrodielectric or electromagnetic induction heating of tissue itself. In this invention, the difference in magnitude of electroconductivity or magnetic permeability between the particle and the tissue is utilized so as to heat the particle exclusively or much faster than tissue. Very short, almost instantaneous pulsive heating is preferable in order to prevent the adhered HIVs/infected cells to separate from the particle. Particles can be heated as high as 100° C. because heat spot is micro-local and kept only in short time. However, spaciously averaged temperature after thermal diffusion should not exceed 42° C., the maximum allowed temperature to tissue.

Alternating magnetic field provides mechanical vibration to the magnetic particles and mechanical shear and heat to the HIVs/infected cells adhered to the particles resulting from the viscosity of body fluid. Thus, HIVs and infected cells are destroyed.

The electromagnetic field can be applied with a long solenoid coil or magnetic gap, into which the entire body is inserted or with a short solenoid coil or magnetic gap through which the entire body is transferred. The former is preferable, considering fairly rapid body fluid flow. The long solenoid coil or magnetic gap can be replaced by a number of short coils or magnetic gaps placed in line and driven in parallel with electromagnetic power source. The short coils (magnetics) connected in parallel can reduce the inductance, hence the time constant also. A short time constant is preferable for pulsive operation.

The apparatuses and medicaments particularly used in the methods of this invention are included in the scope of this invention.

Although the foregoing invention has been described with reference to its preferred embodiments, various alterations and modifications will occur to those skilled in the art. All such alterations and modifications are intended to fall within the scope of the appended claims.

We claim:

1. A method for treating a body fluid related disease in a body where a retrovirus is present in the body fluid and in cells infected by the retrovirus, comprising the steps of:

administering as a Trigger Factor a substance that stimulates the region of proliferation control in the retrovirus in an infected cell to increase proliferation rate, shorten cell life, and cause transition from an asymptomatic period to a symptomatic period, to induce death of the infected cells, withdrawing the body fluid, extracorporeally processing the withdrawn body fluid to kill, inactivate, or remove the pathogenic microorganisms and preferably the infected cells present in the body fluid, and reinfusing the processed body fluid wherein the Trigger Factor is administered either prior to or in parallel with the withdrawing and processing steps.

2. The method of claim 1 wherein the retrovirus is an HIV.

3. The method of claim 1 wherein the processing step includes extra corporeally processing the body fluid as a whole.

4. The method of claim 1 where the processing step includes separating the body fluid into fractions based on at least one characteristic selected from the group consisting of size, shape, mass, electromagnetic characteristics, thermal characteristics, and electrochemical characteristics.

5. The method of claim 4 further comprising the steps of:

further processing the withdrawn body fluid to replace the body fluid fraction containing the microorganism and infected cells with a healthy body fluid fraction, and recombining the processed fractions of body fluid and unprocessed fractions of body fluid for reinfusion.

6. The method of claim 2 where the infected cell is a CD4 (positive) cell selected from the group consisting of T4 Helper lymphocytes, macrophages and dendritic cells, into which the RNA of the HIV has been transcribed and inserted as a provirus;

wherein the body fluid is a fluid selected from the group consisting of blood, lymphatic fluid and cerebrospinal fluid; and wherein the Trigger Factor is a substance selected from the group consisting of a biochemical substance and a medicament.

7. The method of claim 6 where the biochemical substance stimulates the provirus in the infected cell to replicate actively, subjects the infected cell to programmed death, and promotes a transition from a latent period to the AIDS related complex (ARC) period.

8. The method of claim 7 where the biochemical substance is a substance selected from the group consisting of Tumor Necrosis Factor (TNF) and anti-Fas antibody.

9. The method of claim 6 where the medicament subjects the infected cell to death while differentiating infected from healthy cells, but is not adequate to treat AIDS due to stimulated HIV replication during the period prior to death.

10. The method of claim 2 further comprising administering a chemical agent to inhibit or suppress new infection of healthy cells by HIV.

11. The method of claim 10 wherein the chemical agent is selected from the group consisting of soluble CD4 to inhibit infectious adhesion; AZT, ddI and ddC to inhibit reverse transcription and a medicament that inhibits release of replicated HIV from the infected cell.

12. The method of claim 2 further comprising raising the temperature of the body to inhibit or suppress new infection of healthy cells by HIV.

13. The method of claim 12 also including the step of raising the body temperature by administering a fever raising microorganism.

14. The method of claim 12 also including the step of raising the body temperature by administering biochemical agents induced by microorganisms selected from the group consisting of malaria and typhoid.

15. The method of claim 12 also including a step of raising the body temperature by the application of external sources of heat where the sources are selected from the group consisting of hyperthermia or blood heating.

16. The method of claim 1 further comprising the steps of:

removing and neutralizing any reagents added and toxic substances generated during the processing.

* * * * *